United States Patent [19]

Shimomura et al.

[11] Patent Number: 4,959,060
[45] Date of Patent: Sep. 25, 1990

[54] BODY FLUID-ADSORBING ARTICLE

[75] Inventors: Tadao Shimomura, Toyonaka; Nobuyuki Harada; Kunihiko Ishizaki, both of Suita, all of Japan

[73] Assignee: Nippon Shokubai Kagaku Kogyo Co., Ltd., Osaka, Japan

[21] Appl. No.: 449,456

[22] Filed: Dec. 12, 1989

Related U.S. Application Data

[63] Continuation of Ser. No. 121,275, Nov. 16, 1987, abandoned.

[30] Foreign Application Priority Data

Nov. 17, 1986 [JP] Japan .................. 61-271963
Dec. 16, 1986 [JP] Japan .................. 61-297517
Dec. 17, 1986 [JP] Japan .................. 61-298986

[51] Int. Cl.$^5$ ............................................ A61F 13/00
[52] U.S. Cl. ................................................ 604/368
[58] Field of Search .............. 604/368, 358, 365, 366, 604/367, 369, 370, 374

[56] References Cited

U.S. PATENT DOCUMENTS

| | | |
|---|---|---|
| 3,661,815 | 5/1972 | Smith . |
| 3,669,103 | 6/1972 | Harper et al. . |
| 3,670,731 | 6/1972 | Harmon . |
| 4,076,663 | 2/1978 | Masuda et al. . |
| 4,102,340 | 7/1978 | Mesck et al. . |
| 4,235,237 | 11/1986 | Mesek et al. .................. 604/368 |
| 4,286,082 | 8/1981 | Tsubakimoto et al. . |
| 4,363,322 | 12/1982 | Andersson . |
| 4,364,992 | 12/1982 | Ito et al. . |
| 4,610,678 | 9/1986 | Weisman et al. . |
| 4,654,039 | 3/1987 | Brandt et al. .................. 604/368 |
| 4,666,975 | 5/1987 | Yamasaki et al. . |
| 4,683,274 | 7/1987 | Nakamura et al. . |

FOREIGN PATENT DOCUMENTS

| | | |
|---|---|---|
| 0249391 | 12/1987 | European Pat. Off. . |
| 2914386 | 10/1979 | Fed. Rep. of Germany . |
| 52-14689 | 2/1977 | Japan . |
| 53-15959 | 5/1978 | Japan . |
| 62-225507 | 10/1987 | Japan . |
| 2022505 | 12/1979 | United Kingdom . |

Primary Examiner—C. Fred Rosenbaum
Assistant Examiner—Kathleen A. Daley
Attorney, Agent, or Firm—Burns, Doane, Swecker & Mathis

[57] ABSTRACT

A body fluid-absorbing article such as, for example, a disposable diaper is provided with at least one absorbent member comprising 50 to 99% by weight of a fibrous material and 50 to 1% by weight of an absorbent polymer, which absorbent member contains at least one compound (A) selected from the group consisting of sulfur-containing reducing agents, antioxidants, and oxidizing agents. By the action of the compound (A), the swelled gel of the absorbent polymer formed in consequence of absorption of body fluid is prevented from being deteriorated or decomposed by aging.

21 Claims, No Drawings

BODY FLUID-ADSORBING ARTICLE

This application is a continuation of application Ser. No. 121,275, filed Nov. 16, 1987, now abandoned.

BACKGROUND OF THE INVENTION

1. Field of the Invention:

This invention relates to a body fluid-absorbing article using a specific absorbent member containing an absorbent polymer. More particularly, it relates to a body fluid-absorbing article possessing notably improved absorption properties such that even after absorption of body fluid, the absorbed body fluid is stably retained long therein without suffering leakage sideways.

2. Description of the Prior Art:

As absorbent members for such body fluid-absorbing articles as disposable diapers, sanitary napkins, and sweat-absorbing pads, the products obtained by combining such fibrous materials as cotton, pulp, and paper with absorbent polymers as disclosed in U.S. Pat. Nos. 3,669,103; 3,670,731; 4,102,340; 4,364,992; and 4,610,678 have been in popular use in recent years. From the standpoint of ensuring ease of carriage and comfort of wear, these absorbent articles are tending toward reduction of size. In the circumstances, absorbent articles which incorporate therein absorbent polymers in increasingly large proportions have been appearing in increasing volumes in the market.

In the conventional body fluid-absorbing articles which use absorbent members incorporating therein absorbent polymers, however, no due attention has been paid to the prevention of absorbent polymers used therein from being deteriorated and decomposed by the absorbed body fluid, though numerous uniquely devised constructions have been proposed for use in such body fluid-absorbing articles as disclosed in the aforementioned patent publications. When they absorb such body fluids as urine, menstrual blood, and sweat, the swelled gel of the absorbent polymer in the absorbent member gradually undergoes deterioration and decomposition even to a point where the absorbent member is no longer able to retain the absorbed body fluid stably and present sideways leakage of the body fluid, often with the result that the leaking body fluid will smear bedclothes and clothing.

As means of preventing the absorbent polymer from being deteriorated and decomposed by the absorbed body fluid, U.S. Patent No. 4,666,975, for example, has proposed a method for improving the stability of the swelled gel by allowing the particles of the absorbent polymer to assume an increased cross-linking density in the surface region thereof. The absorbent polymer obtained by this method, however, suffers inevitably from a decrease in the capacity thereof for holding the absorbed body fluid. Thus, the absorbent polymer has found utility in absorbent members for body fluid-absorbing articles only with difficulty.

As described above, the conventional body fluid-absorbing articles have posed a problem in the sense that the ability of the absorbent member to retain the absorbed body fluid is degraded with elapse of time even to a point where the sideways leakage of the absorbed body fluid will become inevitable. In the circumstances, the desirability of developing a body fluid-absorbing article . of improved absorption properties incorporating therein an absorbent polymer-containing absorbent member excellent in ability to retain the absorbed body fluid stably for a long time has been finding growing recognition.

An object of the present invention, therefore, is to provide a novel body fluid-absorbing article.

Another object of this invention is to provide a body fluid-absorbing article of improved absorption properties incorporating therein an absorbent member excellent in ability to retain the absorbed body fluid for a long time.

SUMMARY OF THE INVENTION

The objects described above are accomplished by a body fluid-absorbing article which is provided with at least one absorbent member comprising 50 to 99% by weight of a fibrous material and 50 to 1% by weight of an absorbent polymer, which absorbent member contains at least one compound (A) selected from the group consisting of sulfur-containing reducing agents, antioxidants, and oxidizing agents.

As the result of our study, we have found that, after the body fluid-absorbing article has absorbed the body fluid, the aforementioned compound (A) is capable of preventing the swelled gel of the absorbent polymer from being deteriorated or decomposed with elapse of time.

DESCRIPTION OF THE PREFERRED EMBODIMENT

In this invention, the absorbent polymer as a component of the body fluid absorbent member has such nature that, on immersion in water, it will absorb a large volume of water and swell and consequently form a substantially water-insoluble hydrogel. As typical examples of the absorbent polymer of this description, there can be cited hydrolyzed starch-acrylonitrile graft polymer, partially neutralized starch-acrylic acid graft polymer, saponified vinyl acetate-acrylic ester copolymer, hydrolyzates of acrylonitorile copolymers, cross-linked hydrolyzates of acrylonitrile copolymers, hydrolyzates of acrylamide copolymers, cross-linked hydrolyzates of acrylamide copolymers, partially neutralized polyacrylic acid, cross-linked partially neutralized polyacrylic acid, and isobutylene-maleic anhydride copolymer.

These absorbent polymers in themselves are well known to persons of ordinary skill in the art. They are disclosed as in U.S. Pat. Nos. 4,286,082; 3,661,815; 4,076,663; and 4,683,274, Japanese Patent Laid-Open SHO 52(1977)-14,689, and Japanese Patent Publication SHO 53(1978)-15,959.

Examples of the fibrous material which is one of the components of the body fluid absorbent member include such synthetic fibers as polyamide, polyacrylonitrile, polyester, and polyolefins and such cellulosic fibers as cotton, rayon, and pulp. In the absorbent member, this fibrous material is used in the form of long-staple fibers or short-staple fibers or in the form of sheet such as paper, non-woven fabric, woven fabric, or knit fabric which is obtained by interlacing such fibers. Among other fibrous materials cited above, cellulosic fibers are used most advantageouly from the standpoint of the absorption properties of the absorbent member to be eventually produced. From the standpoint of ease of handling during the course of the fabrication of the absorbent member, use of ground pulp, ground pulp sheet, or tissue paper proves to be desirable.

The sulfur-containing reducing agent which is used as the compound to be contained in the body fluid absorbent member of the present invention is not specifically restricted so long as it is a sulfur compound capable of the reaction of reduction. Examples of the sulfur-containing reducing agent include sulfides such as ammonium sulfide, sodium sulfide, potassium sulfide, and lithium sulfide; hydrosulfides such as sodium hydrosulfide; sulfur oxide compounds such as thiosulfates represented by sodium thiosulfate and potassium thiosulfate, sulfurous acid, sulfites represented by sodium sulfite and potassium sulfite, hydrogen sulfites represented by sodium hydrogen sulfite and potassium hydrogen sulfite, and dithionites represented by hydrosulfite; and mercaptans such as mercaptoethanol, cysteine, and alkyl mercaptans represented by methyl mercaptan, ethyl mercaptan, propyl mercaptan and butyl mercaptan.

The antioxidant to be used as the compound (A) in the present invention is not specifically restricted. Examples of the antioxidant include water-soluble antioxidants such as citric acid, pyrogallol, 1,1-bis(4-hydroxyphenol)-cyclohexane, hydroquinone, 8-naphthol, and ethyl gallate; phenol type antioxidants such as 2,6-di-t-butyl-p-cresol and butylated hydroxyanisol; sulfur-containing antioxidants such as thiourea dioxide and dilauryl thiodipropionate; and phosphorus-containing antioxidants such as triphenyl phosphite.

Examples of the oxidizing agent to be used as the compound (A) in the present invention include peroxides such as hydrogen peroxide, sodium peroxide, and barium peroxide; halogens such as fluorine, chlorine, bromine, and iodine; metal salts such as ferric chloride, cupric sulfate, cupric chloride, cupric acetate, and lead (II) acetate; metal oxides such as potassium permanganate, potassium chromate, potassium dichromate, and osmium tetraoxide; halogen oxides such as sodium hypochlorite, potassium hypochlorite, sodium chlorite, chlorine dioxide, chloramine T, bleaching powder, perchloric acid, sodium perchlorate, periodic acid, sodium periodate, and potassium periodate; and quinones such as p-benzoquinone.

Among the examples of the compound (A) cited above, sulfur-containing reducing agents which are highly effective in preventing the swelled gel of the absorbent polymer formed by absorption of body fluid from being deteriorated with time prove to be particularly desirable.

In the present invention, the compound (A) is desired to be contained in the body fluid absorbent member in an amount in the range of 0.05 to 20 parts by weight, preferably 0.1 to 10 parts by weight, based on 100 parts by weight of the absorbent polymer. If the amount of the compound (A) is less than 0.05 part by weight, it is not enough for the compound (A) to manifest any substantial effect in preventing the swelled gel of the absorbent polymer from being deteriorated with time. If the amount exceeds 20 parts by weight, the excess does not produce any proportionate addition to the effect but rather goes to decreasing the capacity of the absorbent member for absorbing the body fluid. Any deviation from the aforementioned range is not desirable.

The body fluid-absorbing article of the present invention is formed by incorporating the aforementioned compound (A) in at least one body fluid absorbent member which consists of 50 to 99% by weight, preferably 60 to 90% by weight, of a fibrous material and 50 to 1% by weight, preferably 40 to 10% by weight, of an absorbent polymer. The present invention does not discriminate the body fluid-absorbing article on account of the shape of the absorbent member or the condition of distribution of the components in the absorbent member. It can be produced, therefore, by using any of the conventional methods adaptable for the fabrication of an absorbent polymer in an absorbent member prepared in any form such as sheet or film which is convenient for the manufacture of a body fluid-adsorbing article such as, for example, disposable diaper, sanitary napkin, or sweat pad. To be specific, the absorbent member can be obtained by having an absorbent polymer nipped between sheets of fibrous material or by mixing an absorbent polymer with ground fibrous material and subsequently molding the resultant mixture in the form of a sheet.

The means employed for the incorporation of the compound (A) in the absorbent member is not specifically restricted so long as it is capable of depositing the compound (A), preferably uniformly, in the absorbent member lest it should fall off the absorbent member. For example, this incorporation may be accomplished during the course of the manufacture of the absorbent member by simply adding the compound (A) to either of the absorbent polymer and the fibrous material such as paper or pulp which are the components of the absorbent member. This addition of the compound (A) can be attained by directly adding the compound (A) in its unmodified powdery form or by dissolving or dispersing the compound (A) in a suitable vehicle such as water or an organic solvent, spraying the resultant liquid preparation on the absorbent member or impregnating the absorbent member with the liquid preparation, and drying the wet absorbent member, when necessary, to expel the vehicle.

Examples of the method for the incorporation of the compound (A) in the body fluid-absorbent member are as follows:

(1) A method which causes the compound (A) to be incorporated in the absorbent member after the pattern of sandwich by preparing a mixture of an absorbent polymer with the compound (A) in a powdered form and having the mixture interposed in the form of layer between at least two sheets of the fibrous material.

(2) A method which causes the compound (A) to be homogeneously incorporated throughout the absorbent member by preparing a mixture of the absorbent polymer, the compound (A) in a powdered form, and short-staple fibers as a fibrous material and air molding the mixture in the form of sheet.

(3) A method which causes the compound (A) to be contained in layers in the absorbent member by spraying a solution or dispersion of the compound (A) on the absorbent polymer then drying the wet absorbent polymer, when necessary, thereby producing a composite having the compound (A) deposited on the absorbent polymer, and then having this composite interposed between at least two sheets of the fibrous material.

(4) A method which causes the compound (A) to be uniformly contained in the absorbent member by spraying a solution or dispersion of the compound (A) on the absorbent polymer, then drying the wet absorbent polymer, when necessary, thereby producing a composite having the compound (A) deposited on the absorbent polymer, mixing the composite with short-staple fibers as the fibrous material, and air laying the resultant mixture in the form of sheet.

(5) A method which causes the compound(A) to be contained in layers in the absorbent member by spraying a solution or dispersion of the compound (A) on at least one sheet of the fibrous material, then drying the wet sheet, when necessary, thereby producing sheet of the fibrous material having the compound (A) deposited thereon, and having the absorbent polymer interposed between the sheet of the fibrous material.

(6) A method which causes the compound (A) to be uniformly contained in the absorbent member by spraying a solution or dispersion of the compound (A) on short-staple fibers as the fibrous material, drying the wet short-staple fibers, when necessary, thereby producing a composite having the compound (A) on the short-staple fibers, mixing this composite with the absorbent polymer, and air molding the resultant mixture in the form of sheet.

(7) A method which causes the compound (A) to be contained in layers in the absorbent member by immersing at least two sheets of the fibrous material in a solution or dispersion of the compound (A), then drying the wet sheets, when necessary, thereby allowing the compound (A) to be deposited on the sheets, and having the absorbent polymer interposed between the two sheets of the fibrous material after the pattern of sandwich.

In all the conceivable solutions of the compound (A), the aqueous solution proves to be particularly desirable from the standpoint of ease of the handling. In all the conceivable sheets of fibrous material, the sheet of ground pulp and the tissue paper prove to be particularly desirable. Among other possible forms of short-staple fibers, the ground pulp proves to be desirable.

The production of the body fluid-absorbing article of the present invention from the body fluid absorbent member which is obtained as described above is accomplished by suitably fabricating the absorbent member all by itself or by suitably combining the absorbent member with other components so as to meet the purpose for which the body fluid-absorbing article will be used. To be used as a pad for the absorption of sweat, for example, the body fluid-absorbing article can be obtained simply by placing the absorbent member as obtained on a mat. To be used as a disposable diaper or sanitary napkin, the body fluid-absorbing article can be obtained by having the absorbent member as obtained interposed between a liquid-pervious top sheet and a liquid-impervious back sheet.

The body fluid-absorbing article of the present invention produces the effect thereof particularly advantageously when it is used as a disposable diaper which is destined to remain for a long time in contact with urine, i.e. a body fluid discharged in a large volume and suffered to induce the phenomenon of deterioration and decomposition of the swelled gel of the absorbent polymer particularly conspicuously.

The body fluid-absorbing article of the present invention can be used efficiently as disposable diaper, sanitary napkin, or sweat pad because the absorbent polymer-containing absorbent member neither permits gradual deterioration of the ability thereof to hold the absorbed body fluid nor suffers from sideways leakage of the absorbed body fluid.

Further in the body fluid-absorbing article of the present invention, since the deterioration and decomposition of the absorbent polymer is perfectly curbed even after the absorption of the body fluid owing to the action of the compound (A) contained in the absorbent member, the proportion of the absorbent polymer in the absorbent member can be increased. The present invention, therefore, permits provision of a body fluid-absorbing article which is compact, convenient for carriage, comfortable to wear, and excellent in the absorbing property.

Now, the present invention will be described more specifically below with reference to working examples. It should be noted, however, that the present invention is not limited to these examples. Wherever parts and percents (%) are mentioned in the following examples, they are meant to refer to parts by weight and percents (%) by weight unless otherwise specified.

EXAMPLE 1

A granular absorbent (1) was obtained by mixing 100 parts of an absorbent polymer composed mainly of a cross-linked partially neutralized polyacrylic acid (produced by Nippon Shokubai Kagaku Kogyo Co., Ltd. and marketed under trademark designation of "AQUALIC CA") by spraying with 1 parts of an aqueous 20% sodium thiosulfate solution.

Then, 1.5g of the absorbent (1) was uniformly spread between two sheets of ground pulp 190 mm $\times$ 140 mm in area (having a basis weight of 150 g/m$^2$ and a density of 0.1 g/cm$^3$) after the pattern of sandwich, to produce an absorbent member. This absorbent member was interposed between one polyethylene film and one polypropylene spun-bond non-woven fabric, to produce a body fluid-absorbing article (1) according with the present invention.

Onto the central part of the body fluid-absorbing article (1) on the non-woven fabric side, 60g of adult human urine was poured to be absorbed by the article (1). The body fluid-absorbing article (1) was left standing for 8 hours. After the standing, 10 paper towels 23 cm$\times$23 cm in area were piled up on the non-woven fabric side of the article (1). and kept pressed under 40 g/cm$^2$ for 1 minute. The paper towels were weighed to determine the amount of the portion of adult human urine absorbed by the paper towels from the article (1). The swelled gel in the article (1) was visually examined to rate the degree of deterioration of the absorbent polymer on the three-point (O−Δ−X) scale. The results are shown in Table 1.

CONTROL 1

A body fluid-absorbing article (1) for comparison was obtained by following the procedure of Example 1, excepting 1.5 g of the same absorbent polymer (a product marketed under trademark designation of "AQUALIC CA") as used in Example 1 was used in the place of the same amount of the absorbent (1) of Example 1.

The body fluid-absorbing article (1) for comparison obtained as described above was tested for the ability to hold the absorbed adult urine and for the degree of deterioration of the absorbent polymer by following the procedure of Example 1. The results are shown in Table 1.

EXAMPLE 2

An absorbent (2) was obtained by mixing 100 parts of an absorbent polymer composed mainly of a partially neutralized starch-acrylic acid graft polymer (produced by Sanyo Chemical Industries Co., Ltd. and marketed under trademark designation of "Sunwet IM-1000") with 1 part of powdered sodium sulfite.

A body fluid-absorbing article (2) was obtained by following the procedure of Example 1, excepting the absorbent (2) was used in the place of the absorbent (1) of Example 1.

The body fluid-absorbing article (2) was tested for the ability to hold the absorbed adult urine and for the degree of deterioration of the absorbent polymer by following the procedure of Example 1. The results are shown in Table 1.

CONTROL 2

A body fluid-absorbing article (2) for comparison was obtained by following the procedure of Example 1, excepting 1.5 g of the same absorbent polymer (a product marketed under trademark designation of "Sunwet IM-1000") as used in Example 2 was used in the place of 1.5 g of the absorbent (1) of Example 1.

The body fluid-absorbing article (2) for comparison was tested for the ability to hold the absorbed adult urine and for the degree of deterioration of the absorbent polymer by following the procedure of Example 1. The results are shown in Table 1.

EXAMPLE 3

A powdery absorbent (3) was obtained by mixing 100 parts of the same absorbent polymer as used in Example 1 with 1 part of mercapto ethanol by spraying.

A body fluid-absorbing article (3) was obtained by following the procedure of Example 1, excepting the absorbent (3) was used in the place of the absorbent (1) of Example 1.

The body fluid-absorbing article (3) was tested for the ability to hold the absorbed adult urine and for the degree of deterioration of the absorbent polymer by following the procedure of Example 1. The results are shown in Table 1.

EXAMPLE 4

An absorbent (4) was obtained by mixing 100 parts of the same absorbent polymer as used in Example 1 with 0.5 part of powdery sodium hydrogen sulfite and 0.5 part of powdery pyrogallol.

A body fluid-absorbing article (4) was obtained by following the procedure of Example 1, excepting the absorbent (4) was used in the place of the absorbent (1) of Example 1.

The body fluid-absorbing article (4) was tested for the ability to hold the absorbed adult urine and for the degree of deterioration of the absorbent polymer by following the procedure of Example 1. The results are shown in Table 1.

EXAMPLE 5

A granular absorbent (5) was obtained by mixing 100 parts of the same absorbent polymer as used in Example 1 with 0.5 part of powdery sodium sulfite and then mixing the resultant mixture with 0.5 part of an aqueous 35% hydrogen peroxide by spraying.

A body fluid-absorbing article (5) was obtained by following the procedure of Example 1, excepting the absorbent (5) was used in the place of the absorbent (1) of the Example 1.

The body fluid-absorbing article (5) was tested for the ability to hold the absorbed adult urine and for the degree of deterioration of the absorbent polymer by following the procedure of Example 1. The results are shown in Table 1.

EXAMPLE 6

A granular absorbent (6) was obtained by mixing 100 parts of the same absorbent polymer as used in Example 1 with 5 parts of an aqueous 20% citric acid solution by spraying.

A body fluid-absorbing article (6) was obtained by following the procedure of Example 1, excepting the absorbent (6) was used in the place of the absorbent (1) of Example 1.

The body fluid-absorbing article (6) was tested for the ability to hold the absorbed adult urine and for the degree of deterioration of the absorbent polymer by following the procedure of Example 1. The results are shown in Table 1.

EXAMPLE 7

A granular absorbent (7) was obtained by mixing 100 parts of the same absorbent as used in Example 1 with 50 parts of an aqueous 3% iodine solution by spraying and drying at 80° C for 16 hours in vacuum.

A body fluid-absorbing article (7) was obtained by following the procedure of Example 1, excepting the absorbent (7) was used in the place of the absorbent (1) of Example 1.

The body fluid-absorbing article (7) was tested for the ability to hold the absorbed adult urine and for the degree of deterioration of the absorbent polymer by following the procedure of Example 1. The results are shown in Table 1.

EXAMPLE 8

Two pulp sheets (1) incorporating therein a sulfur-containing reducing agent were obtained by spraying 0.5 g of an aqueous 10% cysteine solution on two sheets of ground pulp 190 mm × 140 mm in area (having a basis weight of 150 g/m$^2$ and a density of 0.1 g/cm$^3$).

Then, 1.5 g of the same absorbent polymer as used in Example 1 was uniformly scattered between the two pulp sheets (1) after the pattern of sandwich, to produce an absorbent member. This absorbent member was interposed between one polyethylene film and one polypropylene spun-bond non-woven fabric, to produce a body fluid-absorbing article (8).

The body fluid-absorbing article (8) was tested for the ability to hold the absorbed adult urine and for the degree of deterioration of the absorbent polymer by following the procedure of Example 1. The results are shown in Table 1.

EXAMPLE 9

A body fluid-absorbing article (9) was obtained by following the procedure of Example 8, excepting 1.5g of the same absorbent (1) as used in Example 1 was used in the place of 1.5 g of the absorbent polymer of Example 8.

The body fluid-absorbing article (9) was tested for the ability to hold the absorbed adult urine and for the degree of deterioration of the absorbent polymer by following the procedure of Example 1. The results are shown in Table 1.

EXAMPLE 10

A body fluid-absorbing article (10) was obtained by following the procedure of Example 8, excepting 1.5 g of the absorbent (3) obtained in Example (3) was used in the place of 1.5 g of the absorbent polymer of Example 8.

The body fluid-absorbing article (10) was tested for the ability to hold the absorbed adult urine and for the degree of deterioration of the absorbent polymer by following the procedure of Example 1. The results are shown in Table 1.

EXAMPLE 11

Two pulp sheets (2) containing an antioxidant were obtained by spraying 1 g of a 1% ethanol solution of butylated hydroxy anisol on two sheets of ground pulp 190 mm×140 mm in area (having a basis weight of 150 g/m² and a density of 0.1 g/cm³).

Then, 1.5 g of the same absorbent polymer as used in Example 1 was uniformly scattered between the two pulp sheets (2) containing the antioxidant after the pattern of sandwich, to produce an absorbent member. A body fluid absorbing article (11) was obtained by interposing the absorbent member between one polyethylene film and one polypropylene spun-bond non-woven fabric.

The body fluid-absorbing article (11) was tested for the ability to hold the absorbed adult urine and for the degree of deterioration of the absorbent polymer by following the procedure of Example 1. The results are shown in Table 1.

EXAMPLE 12

Two oxidizing agent-containing pulp sheets (3) were obtained by spraying 0.1 g of an aqueous 10% sodium hypochlorite solution on two sheets of ground pulp 190 mm×140 mm in area (having a basis weight of 150 g/m² and a density of 0.1 g/cm³). Then, 1.5 g of the same absorbent, polymer as used in Example 1 was uniformly scattered between the two oxidizing agent-containing pulp sheets (3) after the pattern of sandwich, to produce an absorbent member. A body fluid-absorbing article (12) was obtained by interposing the absorbent member between one polyethylene film and one polypropylene spun-bond non-woven fabric.

The body fluid-absorbing article (12) was tested for the ability to hold the absorbed adult urine and for the degree of deterioration of the absorbent polymer by following the procedure of Example 1. The results are shown in Table 1.

EXAMPLE 13

An absorbent member was obtained by mixing 1.5 g of the same absorbent polymer as used in Example 1 with 0.05 g of powdery sodium thiosulfate and 8 g of ground wood pulp fiber in a current of air, leading the resultant mixture over a wire screen of 100 mesh (having an area of 190 mm×140 mm), air molding the mixture by attraction toward the wire screen, and compressing the resultant sheet-like web with an embossing roller to a density of 0.07 g/cm³.

A body fluid-absorbing article (13) was obtained by following the procedure of Example 1, excepting the absorbent member was used in the place of the absorbent member of Example 1.

The body fluid-absorbing article (13) was tested for the ability to hold the absorbed adult urine and for the degree of deterioration of the absorbent polymer by following the procedure of Example 1. The results are shown in Table 1.

EXAMPLE 14

A body fluid-absorbing article (14) was obtained by following the procedure of Example 13, excepting 1.5 g of the absorbent (4) obtained in Example 4 was used in the place of 1.5 g of the absorbent polymer of Example 13.

The body fluid-absorbing article (14) was tested for the ability to hold the absorbed adult urine and for the degree of deterioration of the absorbent polymer by following the procedure of Example 1. The results are shown in Table 1.

TABLE 1

| Body fluid-absorbing article | Amount of adult urine absorbed out (g) | Degree of deterioration of absorbent polymer (Note 1) |
| --- | --- | --- |
| Example 1 Article (1) | 1.8 | O |
| Control 1 Article (1) for comparison | 8.1 | X |
| Example 2 Article (2) | 2.7 | O |
| Control 2 Article (2) for comparison | 10.7 | X |
| Example 3 Article (3) | 1.7 | O |
| Example 4 Article (4) | 2.0 | O |
| Example 5 Article (5) | 2.1 | O |
| Example 6 Article (6) | 2.4 | O |
| Example 7 Article (7) | 2.4 | O |
| Example 8 Article (8) | 1.9 | O |
| Example 9 Article (9) | 1.6 | O |
| Example 10 Article (10) | 1.5 | O |
| Example 11 Article (11) | 2.5 | O |
| Example 12 Article (12) | 2.3 | O |
| Example 13 Article (13) | 1.5 | O |
| Example 14 Article (14) | 1.4 | O |

(Note 1)
O: Perfectly retained shape of swelled gel.
Δ: Partially broken shape of swelled gel.
X: Totally broken shape of swelled gel into slurry state.

EXAMPLE 15

A granular absorbent (8) was obtained by mixing 100 parts of the same absorbent polymer as used in Example 1 with 5 parts of an aqueous 20% potassium hydrogen sulfite by spraying and then drying the resultant mixture at 80° C. for 30 minutes. An absorbent member was obtained by mixing 1.5 g of the absorbent (8) with 8 g of ground wood pulp fibers in a current of air, leading the resultant mixture over a wire screen of 100 mesh (having an area of 190 mm×140 mm) and air molding the mixture by attraction toward the wire screen, and compressing the resultant sheet-like web with an embossing roller to a density of 0.07 g/cm³ A body fluid-absorbing article (15) was obtained by wrapping the absorbent member with tissue paper and interposing the wrapped absorbent member between one polyethylene film and one polypropylene spun-bond non-woven fabric.

Onto the central part of the body fluid-absorbing article (15) on the non-woven fabric side, 60 g of adult human urine was poured to be absorbed by the article (15). The body fluid-absorbing article (15) was left standing for 16 hours. After the standing, 10 paper towels 23 cm×23 cm in area were piled up on the non-woven fabric side of the article (15) and kept pressed under 40 g/cm² for 1 minute. The paper towels were weighed to determined the amount of the portion of adult human urine absorbed by the paper towels from the article (15). The swelled gel in the article (15) was visually examined to rate the degree of deterioration of the absorbent polymer on the three-point (O−Δ−X) scale. The results are shown in Table 2.

CONTROL 3

A body fluid-absorbing article (3) for comparison was obtained by following the procedure of Example 15, excepting 1.5 g of the same absorbent polymer (a product marketed under trademark designation of "AQUA-LICK CA") as used in Example 1 was used in the place of 1.5 g of the absorbent (8) of Example 15.

The body fluid-absorbing article (3) for comparison was tested for the ability to hold the absorbed adult urine and for the degree of deterioration of the absorbent polymer by following the procedure of Example 15. The results are shown in Table 2.

EXAMPLE 16

A granular absorbent (9) was obtained by mixing 100 parts of the same absorbent polymer as used in Example 1 with 3 parts of an aqueous 35% hydrogen peroxide solution by spraying.

A body fluid-absorbing article (16) was obtained by following the procedure of Example 15, excepting the absorbent (9) was used in the place of the absorbent (8) of Example 15.

The body fluid-absorbing article (16) was tested for the ability to hold the absorbed adult urine and for the degree of deterioration of the absorbent polymer by following the procedure of Example 15. The results are shown in Table 2.

EXAMPLE 17

An absorbent (10) was obtained by mixing 100 parts of the same absorbent polymer as used in Example 1 with 1 part of ethyl gallate.

A body fluid-absorbing article (17) was obtained by following the procedure of Example 15, excepting the absorbent (10) was used in the place of the absorbent (8) of Example 15.

The body fluid-absorbing article (17) was tested for the ability to hold the absorbed adult urine and for the degree of deterioration of the absorbent polymer by following the procedure of Example 15. The results are shown in Table 2.

EXAMPLE 18

An absorbent member was obtained by spray mixing 100 parts of ground pulp with 5 parts of an aqueous 20% sodium hydrogen sulfite, drying the resultant mixture at 80° C. for 2 hours thereby producing ground pulp having a sulfur-containing reducing agent deposited thereon, mixing 8 g of the ground pulp with 1.5 g of the same absorbent polymer as used in Example 15 in a current of air, then air molding the resultant mixture in the same manner as in Example 15, and compressing the resultant sheet-like web with an embossing roller to a density of 0.07 g/cm$^3$.

A body fluid-absorbing article (18) was obtained by wrapping the absorbent member with tissue paper and interposing the wrapped absorbent member between one polyethylene film and one polypropylene spun-bond non-woven fabric.

The body fluid-absorbing article (18) was tested for the ability to hold the absorbed adult urine and for the degree of deterioration of the absorbent polymer by following the procedure of Example 15. The results are shown in Table 2.

EXAMPLE 19

An absorbent member was obtained by uniformly scattering 1.5 g of the absorbent (1) obtained in Example 1 between two sheets of tissue paper 190 mm × 140 mm in area, pressing the resultant composite with an embossing roller thereby producing an absorbent polymer sheet (1), and superposing two sheets of ground pulp 190 mm × 140 mm in area (having a basis weight of 150 g/m$^2$ and a density of 0.1 g/cm$^3$) one each on the opposite sides of the polymer sheet(1).

A body fluid-absorbing article (19) was obtained by interposing the absorbent member between one polyethylene film and one polypropylene spun-bond non-woven fabric.

The body fluid-absorbing article (19) was tested for the ability to hold the absorbed adult urine and for the degree of deterioration of the absorbent polymer by following the procedure of Example 15. The results are shown in Table 2.

EXAMPLE 20

Two sheets of tissue paper 190 mm × 140 mm in area (having a basis weight of 20 g/m$^2$) was immersed in an aqueous 0.5% sodium sulfite solution and then dried at 80° C. under a vacuum to produce two sheets of tissue paper having a sulfur-containing reducing agent deposited thereon. The amount of sodium sulfite deposited thereon, determined on the basis of one of the immersed sheets of tissue paper, was found to be 0.02 g. An absorbent polymer sheet (2) was obtained by scattering 1.5 g of the same absorbent polymer as used in Example 1 between the two sheets of tissue paper and then compressing the resultant composite with an embossing roller. An absorbent member was obtained by interposing this polymer sheet (2) between two sheets of ground pulp 190 mm × 140 mm in area (having a basis weight of 150 g/m$^2$ and a density of 0.1 g/cm$^3$).

A body fluid-absorbing article (20) was obtained by interposing the absorbent member between one polyethylene film and one polypropylene spun-bond non-woven fabric.

The body fluid-absorbing article (20) was tested for the ability to hold the absorbed adult urine and for the degree of deterioration of the absorbent polymer by following the procedure of Example 15. The results are shown in Table 2.

TABLE 2

| | Body fluid-absorbing article | Amount of adult urine absorbed out (g) | Degree of deterioration of absorbent polymer (Note 1) |
|---|---|---|---|
| Example 15 | Article (15) | 2.7 | O |
| Control 3 | Article (3) for comparison | 10.2 | X |
| Example 16 | Article (16) | 6.7 | Δ |
| Example 17 | Article (17) | 5.5 | Δ |
| Example 18 | Article (18) | 3.2 | O |
| Example 19 | Article (19) | 3.5 | O |
| Example 20 | Article (20) | 2.9 | O |

(Note 1)
O: Perfectly retained shape of swelled gel.
Δ: Partially broken shape of swelled gel.
X: Totally broken shape of swelled gel into slurry state.

What is claimed is:
1. A body fluid-absorbing article comprising at least one absorbent member which forms a swelled gel when a body fluid is absorbed, comprising 50 to 99% by weight of a fibrous material and 50 to 1% by weight of an absorbent polymer, wherein said absorbent polymer is at least one member selected from the group consisting of hydrolyzed starch-acrylonitrile graft polymer, partially neutralized starch-acrylic acid graft polymer, saponified vinyl acetate-acrylic ester copolymer, hydrolyzed acrylonitrile copolymers, cross-linked hydrolyzed acrylonitrile copolymers, hydrolyzed acrylamide copolymers, cross-linked hydrolyzed acrylamide copolymers, partially neutralized polyarcylic acid, cross-linked partially neutralized polyacrylic acid, and isobutylene-maleic anhydride copolymer, said absorbent member containing at least one species compound (A) selected from the group consisting of sulfur-containing reducing agents, antioxidants, and oxidizing agents, wherein said sulfur-containing reducing agent is at least one member selected from the group consisting of thiosulfates, sulfurous acid, sulfites, hydrogen sulfites dithionites, hydrosulfides, and mercaptans, and said compound (A) being present in a physical mixture with said absorbent polymer in an amount capable of preventing the swelled gel of the absorbent polymer from being deteriorated or decomposed with an elapse of time.

2. An article according to claim 1, wherein said compound (A) is contained in said absorbent member in a ratio falling in the range of 0.05 to 20 parts by weight, based on 100 parts by weight of said absorbent polymer.

3. An article according to claim 1, wherein said compound (A) contains a sulfur-containing reducing agent as an essential component.

4. An article according to claim 3, wherein said compound (A) is a sulfur-containing reducing agent.

5. An article according to claim 4, wherein said sulfur-containing reducing agent is at least one member selected from the group consisting of thiosulfates, sulfites, hydrogen sulfites, and mercaptans.

6. An article according to claim 1, wherein said fibrous material is a cellulosic fiber material.

7. An article according to claim 1, wherein said absorbent polymer is a cross-linked partially neutralized polyacrylic acid.

8. An article according to claim 1, wherein said absorbent polymer and said compound (A) are in the form of a powder mixture interposed between at least two sheets of said fibrous material after the pattern of a sandwich.

9. An article according to claim 1, wherein said absorbent member is an air-molded mixture of said absorbent polymer with said compound (A) in the form of a powder and said fibrous material in the form of short-staple fibers, said absorbent member being in the form of a sheet.

10. An article according to claim 1, wherein said absorbent member is a composite having said compound (A) deposited on said absorbent polymer, said composite being interposed between at least two sheets of said fibrous material after the pattern of a sandwich.

11. An article according to claim 1, wherein said absorbent member is an air molded mixture of a composite having said compound (A) deposited on said absorbent polymer and said fibrous material in the form of short-staple fibers, the air molded mixture being in the form of a sheet containing said compound (A) in a uniformly distributed state.

12. An article according to claim 1, wherein said absorbent member comprises at least two sheets of said fibrous material having said compound (A) deposited on said sheets, said absorbent polymer being interposed between said two sheets after the pattern of a sandwich.

13. An article according to claim 1, wherein said absorbent member is an air molded mixture of a composite having said compound (A) deposited on fibrous material in the form of short-staple fibers and an absorbent polymer said air molded mixture being in the form of a sheet containing said compounds (A) in a uniformly distributed state.

14. An article according to claim 1, wherein said absorbent member comprises at least two sheets of said fibrous material having said compound (A) deposited on said two sheets and said absorbent polymer interposed between said two sheets of said fibrous material after the pattern of a sandwich.

15. An article according to claims 10, 11, 12, 13 or 14, wherein said compound (A) is used in the form of an aqueous solution.

16. An article according to claims 8, 10, 12, or 14, wherein said sheets of fibrous material are made of at least one member selected from the group consisting of ground pulp and tissue paper.

17. An article according to claims 9, 11 or 13, wherein said fibrous material in the form of short-staple fibers is ground pulp.

18. An article according to claim 1, wherein said absorbent member is interposed between a back sheet impervious to body fluid and a top sheet pervious to body fluid.

19. An article according to claim 1, which is a disposable diaper.

20. An article according to claim 1, wherein said absorbent polymer is used in an amount falling in the range of 40 to 10% by weight, based on 60 to 90% by weight of said fibrous material.

21. An article according to claim 1, wherein said compound (A) is contained in said absorbent member in an amount falling in the range of 0.1 to 10 parts by weight, based on 100 parts by weight of said absorbent polymer

* * * * *